United States Patent [19]

LeVaughn et al.

[11] Patent Number: 5,954,738
[45] Date of Patent: Sep. 21, 1999

[54] BLOOD SAMPLING DEVICE WITH LANCET DAMPING SYSTEM

[75] Inventors: Richard W. LeVaughn, McDonough, Ga.; Roger D. Sonnenburg, Osceola, Ind.; William C. Taylor, Rex, Ga.

[73] Assignee: Bayer Corporation, Elkhart, Ind.

[21] Appl. No.: 08/903,697

[22] Filed: Jul. 31, 1997

[51] Int. Cl.$^6$ .................................................. A61B 17/14
[52] U.S. Cl. .................... 606/181; 606/182; 606/183; 606/184; 606/185; 606/186; 604/137; 604/157; 604/240; 604/241
[58] Field of Search ................................. 606/181, 182, 606/184, 185, 186, 183; 604/137, 157, 240, 241

[56] References Cited

U.S. PATENT DOCUMENTS

| | | | |
|---|---|---|---|
| 3,742,954 | 7/1973 | Strickland | 128/302 |
| 4,442,836 | 4/1984 | Meinecke et al. | 128/314 |
| 4,637,403 | 1/1987 | Garcia et al. | 128/770 |
| 4,850,973 | 7/1989 | Jordan et al. | 604/157 |
| 4,976,724 | 12/1990 | Nicto et al. | 606/182 |
| 4,994,068 | 2/1991 | Hufnagle | 606/181 |
| 5,318,584 | 6/1994 | Lange et al. | 606/182 |
| 5,324,303 | 6/1994 | Strong et al. | 606/181 |
| 5,350,392 | 9/1994 | Purcell et al. | 606/182 |
| 5,368,047 | 11/1994 | Suzuki et al. | 128/765 |
| 5,423,847 | 6/1995 | Strong et al. | 606/182 |
| 5,454,828 | 10/1995 | Schraga | 606/181 |
| 5,540,709 | 7/1996 | Ramel | 606/183 |
| 5,662,672 | 9/1997 | Pambianchi et al. | 606/181 |

*Primary Examiner*—Michael Buiz
*Assistant Examiner*—Vy Quang Bui
*Attorney, Agent, or Firm*—Roger Norman Coe

[57] ABSTRACT

A blood sampling device is provided with a housing, a lancet assembly, a lancet holder disposed in the housing for supporting the lancet assembly, the lancet holder being movable in a lancing direction between a cocked position and a puncture position, a drive spring for forcing the lancet holder from the cocked position to the puncture position, and a mechanism for damping movement of the lancet holder during travel of the lancet holder from the puncture position to an intermediate position between the puncture position and the cocked position. The damping mechanism may be provided in the form of a non-planar surface, such as a corrugated surface, disposed on the lancet holder and a damping member which makes contact with the non-planar surface during movement of the lancet holder.

20 Claims, 2 Drawing Sheets

BLOOD SAMPLING DEVICE WITH LANCET DAMPING SYSTEM

BACKGROUND OF THE INVENTION

The present invention relates to a blood sampling device that incorporates a lancet for piercing the skin.

Various types of blood sampling devices for drawing a blood sample from a skin puncture made by a lancet have been described. For example, U.S. Pat. No. 4,517,978 to Levin, et al. discloses a blood sampling device which is provided with a housing, a lancet holder having a lancet with a sharp point, a lancet assembly supported by the lancet holder, and an actuator mechanism for moving the lancet holder from a cocked position to a puncture position and back to an intermediate position between the cocked and puncture positions. Movement of the lancet holder is controlled by a pair of opposed springs, one of which drives the lancet holder from the cocked position to the puncture position and another of which draws the lancet holder from the puncture position to the intermediate position.

One problem with conventional spring-loaded blood sampling devices is the tendency of the lancet holder to oscillate after a puncture is made due to the use of one or more springs for driving the lancet holder. If of a sufficient magnitude, such oscillation could cause, for example, a second puncture to be made after the initial puncture, resulting in unnecessary pain.

A blood sampling device of the type described above is typically used with an industry-standard lancet assembly having a generally cylindrical plastic body, a lancet with a sharp tip and which is supported by the plastic body, and a plastic protective cap attached to the body that covers the tip of the lancet to prevent inadvertent skin puncture prior to use of the blood sampling device. A conventional lancet assembly is shown, for example, in FIG. 6 of U.S. Pat. No. 4,976,724 to Nieto, et al.

SUMMARY OF THE INVENTION

The invention is directed to a blood sampling device having a housing, a lancet assembly, a lancet holder disposed in the housing for supporting the lancet assembly, the lancet holder being movable in a lancing direction between a cocked position and a puncture position, a drive spring for forcing the lancet holder from the cocked position to the puncture position, and means for damping movement of the lancet holder during travel of the lancet holder from the puncture position to an intermediate position between the puncture position and the cocked position.

The damping means may be provided in the form of a non-planar surface disposed on the lancet holder and a damping member which makes contact with the non-planar surface during movement of the lancet holder. The non-planar surface may be a corrugated surface, and the blood sampling device may additionally include means for maintaining the lancet holder in the cocked position and means for releasing the lancet holder from the cocked position to cause the drive spring to force the lancet holder from the cocked position to the puncture position.

The means for maintaining the lancet holder in the cocked position may include a stop member disposed on the lancet holder and a retaining arm which makes contact with the stop member. The means for releasing the lancet holder from the cocked position may include a pushbutton, a release arm operatively connected to the pushbutton, the release arm being movable from a first position to a release position in which the release arm forces the retaining arm away from the stop member, and spring means, such as an elastically deformable foam material, coupled to the pushbutton for biasing the release arm to the first position.

These and other features of the present invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENT

Figure 1:
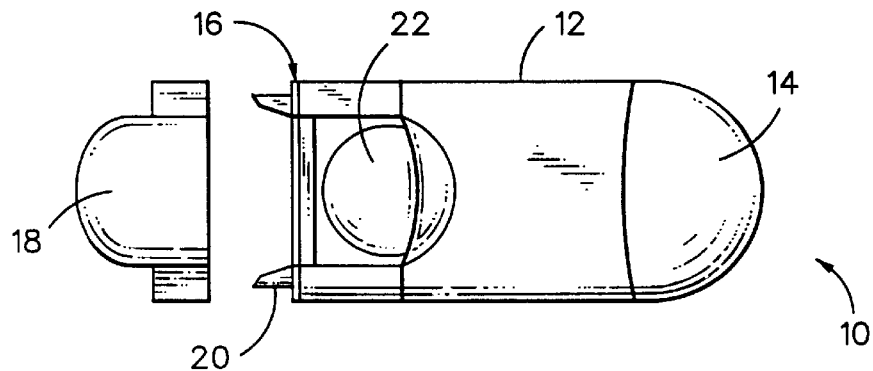
FIG. 1 is a top view of one embodiment of a blood sampling device in accordance with the invention.
Figure 2:
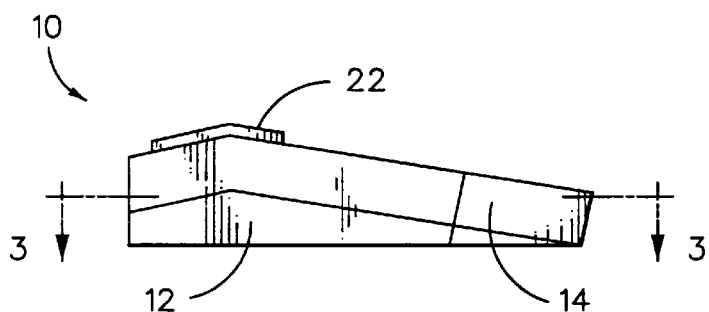
FIG. 2 is a side view of the blood sampling device of FIG. 1.

FIG. 1 illustrates a preferred embodiment of a blood sampling device 10 for taking a sample of blood from a person. Referring to FIG. 1, the blood sampling device 10 has a main housing portion 12, a housing portion 14 movable relative to the main housing 12, an end cap support 16 connected to the main housing 12, and an end cap 18 that may be attached to the end cap support 16 and supported thereon by a pair of support arms 20 integrally formed with the end cap support 18.

When used, the movable housing 14 is pulled away from the main housing 12 to move an internal lancing mechanism to a cocked position, and then a pushbutton 22 is pushed to actuate the lancing mechanism so that the sharp tip of a lancet is forced through a hole (not shown) in the left-hand end of the end cap 18 to cause a skin puncture to be made. The blood sampling device 10 may be provided with a number of different end caps 18, each having a different width, to facilitate the formation of skin punctures of various depths.

Figure 3:
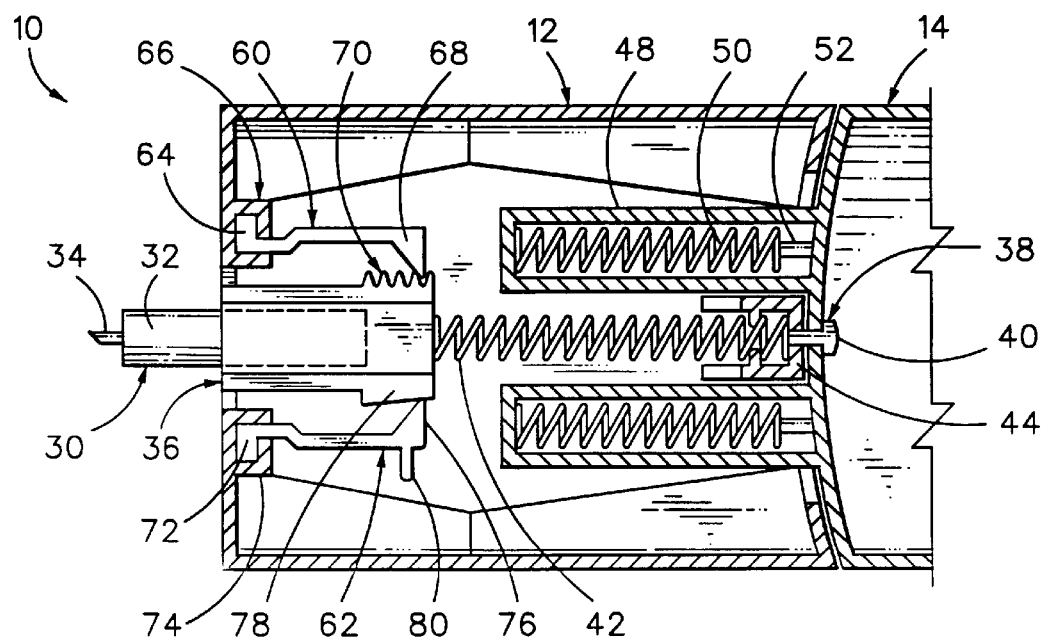
FIG. 3 is a cross-sectional view of a portion of the blood sampling device taken along lines 3—3 of FIG. 2.

FIG. 3 is a cross-sectional view of a portion of the blood sampling device 10 with the end cap 18 and end cap support 16 not shown. Referring to FIG. 3, a lancet assembly 30 having a lancet body 32 (schematically shown) and a lancet 34 is frictionally supported within an internal cylindrical aperture formed in a cup-shaped lancet holder 36 by an interference fit between outer portions of the lancet body 32 and curved inner surfaces in the interior of the lancet holder 36.

The lancet holder 36 is connected to an elongate shaft 38 by being integrally formed therewith. The shaft 38 has an enlarged end 40 which is supported within the movable housing 14. A drive spring 42 is disposed around the shaft 38 between the lancet holder 36 and a C-shaped spring stop 44 (see also FIG. 4) integrally formed with the main housing 12.

The movable housing 14 has a pair of elongate spring trays 48 integrally formed therewith. A return spring 50 is disposed within each of the spring trays 48, the left end of each return spring 50 being disposed against a left-hand internal surface of the spring tray 48 and the right end of each return spring 50 being disposed against a spring stop 52 integrally formed with the main housing 12. The spring stops 52 extend into the spring trays 48 through an elongate slot 54 (see FIG. 4) formed in the bottom portion of each tray 48.

Referring to FIG. 3, a damping arm 60 and a retaining arm 62 are disposed adjacent opposite sides of the lancet holder 36. The damping arm 60 has a first end 64 which is held within a retaining structure 66 integrally formed with the main housing 12 and a second pointed end 68 which is disposed adjacent a corrugated surface 70 formed on an outside portion of the lancet holder 36. The retaining arm 62 has a first end 72 which is held within a retaining structure 74 integrally formed with the main housing 12 and a second pointed end 76 which is disposed adjacent an angled stop member 78. The lower side of the retaining arm 62 rests on a support member 80. The arms 60, 62 are biased inwardly towards the lancet holder 36 so that they make contact with the outer sides of the lancet holder 36.

Figure 4:
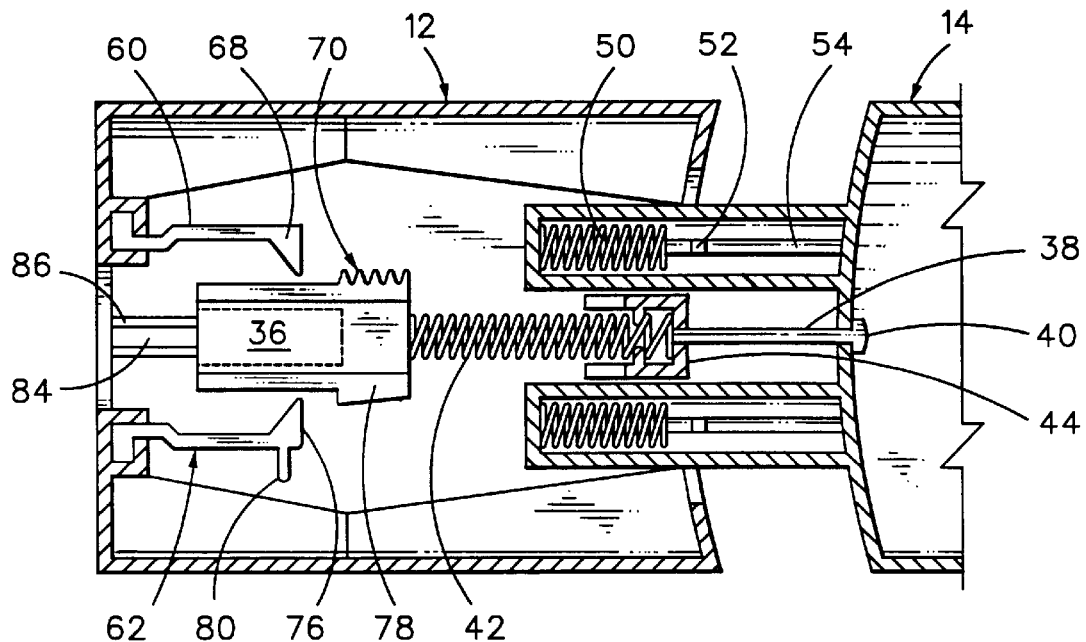
FIG. 4 is a cross-sectional view of the portion of the blood sampling device shown in FIG. 3 when the blood sampling device is in a cocked position.

FIG. 3 shows the interior of the blood sampling device 10 when not in use when the lancet holder 36 is disposed in a resting position between a puncture position and a cocked position. FIG. 4 illustrates the interior of the blood sampling device 10 (the lancet assembly 30 is not shown) when the lancet holder 36 is in a cocked position in which the movable housing 14 has been pulled away from the main housing 12.

Referring to FIG. 4, to move the lancet holder 36 from its resting position to its cocked position, the movable housing 14 is pulled away from the main housing 12, against the force of the drive spring 42, until the angled stop member 78 formed on the lancet holder 36 moves past (to the right of) the pointed end 76 of the retaining arm 62. At that point, the bias of the retaining arm 62 will force its pointed end 76 inwardly, so that the pointed end 76 makes contact with the side of the lancet holder 36 disposed to the left of the angled stop member 78. When in that cocked position, leftward movement of the lancet holder 36 due to the drive spring 42 is prevented due to the contact between the pointed end 76 of the retaining arm 62 and the angled stop member 78. After the lancet holder 36 is placed in the cocked position, the user allows the return springs 50 to force the movable housing 14 back to its initial position adjacent the main housing 12.

The lancet holder 36 is guided between its resting and cocked positions by a guide rib 82 (FIG. 7) formed on the bottom portion of the lancet holder 36 that rides within a groove 84 formed between a pair of raised guide rails 86 formed in a bottom interior portion of the main housing 12.

Figure 5:
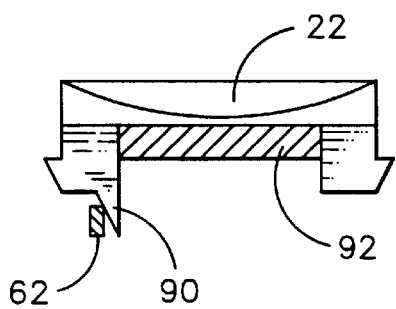
FIG. 5 is a side view of a portion of a release mechanism incorporated within the blood sampling device.

To make a skin puncture, the end cap 18 is attached to the blood sampling device 10 with the lancet holder 36 in the cocked position, the end cap 18 is placed firmly against the skin where the puncture is to be made, and the pushbutton 22 is pressed. Referring to FIGS. 4 and 5, pressing the pushbutton 22 will cause an angled release arm 90 (FIG. 5), integrally formed with the bottom of the pushbutton 22 and which passes through an aperture (not shown) in the main housing 12, to force the retaining arm 62 away from the lancet holder 36 so that leftward movement of the lancet holder 36 is no longer prevented by the contact of the angled stop member 78 with the pointed end 76 of the retaining arm 62. As shown in FIG. 5, spring means in the form of an elastically deformable foam material 92 is disposed between the pushbutton 22 and a portion of the main housing 12 to bias the pushbutton 22 to its non-actuated position.

Upon release of the lancet holder 36 as described above, the drive spring 42 will force the lancet holder 36 to the left in FIG. 4 until the sharp point of the lancet 34 (FIG. 3) passes through the hole (not shown) in the end cap 18 to make the puncture. When the puncture is made, the drive spring 42 will be in a stretched position, and immediately after the puncture is made the contraction of the drive spring 42 will draw the lancet assembly 36 back towards its resting position shown in FIG. 3.

As the lancet holder 36 moves from its puncture position back to its resting position shown in FIG. 3, the pointed tip 68 of the damping arm 60 will make frictional contact with the corrugated surface 70, which frictional contact will decelerate or damp the movement of the lancet holder 36. Such damping prevents the drive spring 42, due to its natural tendency to oscillate (due to its being elastically deformable), from causing a second, unintended skin puncture to be made. As used herein, the term "corrugated" refers to a surface having raised ribs or other structures, either regularly or irregularly spaced, for providing an increased amount of friction when the surface is brought into contact with a damping member.

Figure 7:
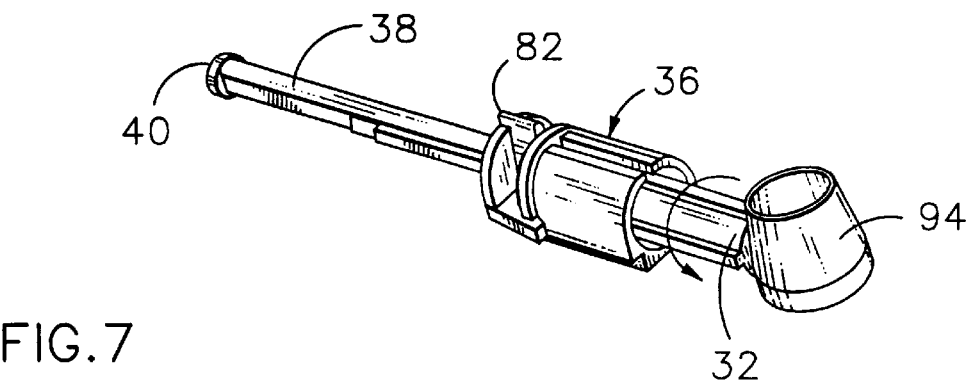
FIG. 7 is a perspective view of the lancet assembly disposed within the lancet holder.

FIG. 7 is a perspective view of the lancet assembly 30 disposed within the lancet holder 36. Referring to FIG. 7, the lancet assembly 30 is shown with a protective cap 94 which has a portion that is integrally formed with the lancet body 32 and which covers the sharp point of the lancet 34. Prior to using the blood sampling device 10, the lancet body 32 of a new lancet assembly 30 is inserted into the cylindrical aperture disposed in the lancet holder 36, and then the protective cap 94 is twisted off of the lancet assembly 30, in the direction of the arrow shown in FIG. 7.

Figure 6:
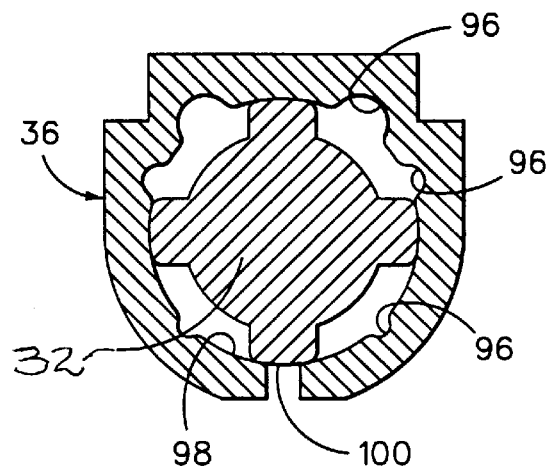
FIG. 6 is a cross-sectional view of a lancet assembly disposed within a lancet holder.

FIG. 6 is an enlarged cross-sectional view of a portion of the lancet body 32 when inserted into the lancet holder 36. Referring to FIG. 6, to prevent significant rotation of the lancet assembly 30 relative to the lancet holder 36 when the protective cap 94 is twisted off, the interior of the lancet holder 36 is provided with six grooves 96, each of the grooves 96 being disposed between an adjacent pair of curved surfaces 98 which together define the cylindrical shape of the internal aperture formed in the lancet holder 36. The edges between the grooves 96 and the curved surfaces 98 act to prevent significant rotation of the lancet body 32 by making contact with four angularly spaced ribs 100 which extend outwardly from a center portion of the lancet body 32.

Because cylindrical aperture formed in the lancet holder 36 is substantially unobstructed by internal ribs or other structures, the lancet body 32 may be inserted into the cylindrical aperture in any angular orientation relative to the lancet holder 36.

All of the components of the blood sampling device 10, except for the springs 42, 50, the lancet 34, and the foam material 92, may be composed of plastic.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A blood sampling device, comprising:
   a housing;
   a lancet assembly;
   a lancet holder disposed in said housing, said lancet holder being adapted to support said lancet assembly, said lancet holder being movable in a lancing direction between a cocked position and a puncture position;
   a drive spring for forcing said lancet holder from said cocked position to said puncture position; and
   means for damping movement of said lancet holder during travel of said lancet holder from said puncture position to an intermediate position between said puncture position and said cocked position, said damping means comprising:
   a corrugated surface disposed on said lancet holder; and
   a damping member which makes contact with said corrugated surface during movement of said lancet holder.

2. A blood sampling device as defined in claim 1 wherein said lancet holder comprises a cup-shaped member and wherein an elongate shaft is connected to said cup-shaped member.

3. A blood sampling device as defined in claim 2 wherein said drive spring is disposed on said elongate shaft between said cup-shaped member and a portion of said housing.

4. A blood sampling device as defined in claim 1 additionally comprising:
   means for maintaining said lancet holder in said cocked position; and
   means for releasing said lancet holder from said cocked position to cause said drive spring to force said lancet holder from said cocked position to said puncture position.

5. A blood sampling device as defined in claim 4 wherein said means for maintaining said lancet holder in said cocked position comprises:
   a stop member disposed on said lancet holder; and
   a retaining arm which makes contact with said stop member.

6. A blood sampling device as defined in claim 5 wherein said means for releasing said lancet holder from said cocked position comprises:
   a pushbutton;
   a release arm operatively connected to said pushbutton, said release arm being movable from a first position to a release position in which said release arm forces said retaining arm away from said stop member; and
   spring means coupled to said pushbutton for biasing said release arm to said first position.

7. A blood sampling device as defined in claim 6 wherein said spring means comprises an elastically deformable foam material.

8. A blood sampling device, comprising:
   a housing;
   a lancet assembly;
   a lancet holder disposed in said housing, said lancet holder being adapted to support said lancet assembly, said lancet holder being movable in a lancing direction between a cocked position and a puncture position;
   a drive spring for forcing said lancet holder from said cocked position to said puncture position; and
   means for damping movement of said lancet holder during travel of said lancet holder from said puncture position to an intermediate position between said puncture position and said cocked position.

9. A blood sampling device as defined in claim 8 where said damping means comprises:
   a non-planar surface disposed on said lancet holder; and
   a damping member which makes contact with said non-planar surface during movement of said lancet holder.

10. A blood sampling device as defined in claim 8 wherein said lancet holder comprises a cup-shaped member and wherein an elongate shaft is connected to said cup-shaped member.

11. A blood sampling device as defined in claim 10 wherein said drive spring is disposed on said elongate shaft between said cup-shaped member and a portion of said housing.

12. A blood sampling device as defined in claim 8 additionally comprising:
    means for maintaining said lancet holder in said cocked position; and
    means for releasing said lancet holder from said cocked position to cause said drive spring to force said lancet holder from said cocked position to said puncture position.

13. A blood sampling device as defined in claim 12 wherein said means for maintaining said lancet holder in said cocked position comprises:
    a stop member disposed on said lancet holder; and
    a retaining arm which makes contact with said stop member.

14. A blood sampling device as defined in claim 13 wherein said means for releasing said lancet holder from said cocked position comprises:
    a pushbutton;
    a release arm operatively connected to said pushbutton, said release arm being movable from a first position to a release position in which said release arm forces said retaining arm away from said stop member; and
    spring means coupled to said pushbutton for biasing said release arm to said first position.

15. A blood sampling device as defined in claim 14 wherein said spring means comprises an elastically deformable foam material.

16. A blood sampling device, comprising:
    a housing;
    a lancet assembly;
    a lancet holder disposed in said housing, said lancet holder having a corrugated surface disposed thereon and being adapted to support said lancet assembly, said lancet holder being movable in a lancing direction between a cocked position and a puncture position;
    spring means for moving said lancet holder through a range of positions including said cocked and puncture positions and an intermediate position disposed between said cocked and puncture positions;
    means for maintaining said lancet holder in said cocked position;
    means for releasing said lancet holder from said cocked position to cause said spring means to force said lancet holder from said cocked position to said puncture position; and
    a damping member which makes contact with said corrugated surface disposed on said lancet holder during movement of said lancet holder.

17. A blood sampling device as defined in claim 16 wherein said means for maintaining said lancet holder in said cocked position comprises:

a stop member disposed on said lancet holder; and a retaining arm which makes contact with said stop member.

18. A blood sampling device as defined in claim 16 wherein said means for releasing said lancet holder from said cocked position comprises:

a pushbutton;

a release arm operatively connected to said pushbutton, said release arm being movable from a first position to a release position in which said release arm forces said retaining arm away from said stop member; and spring means coupled to said pushbutton for biasing said release arm to said first position.

19. A blood sampling device as defined in claim 16 wherein said lancet assembly comprises a lancet having a sharp point and a lancet body for supporting said lancet.

20. A blood sampling device as defined in claim 19 wherein said lancet additionally comprises a protective cap attached to said lancet body for covering said sharp point of said lancet.

* * * * *